United States Patent
Potter et al.

(10) Patent No.: US 11,583,648 B2
(45) Date of Patent: Feb. 21, 2023

(54) HEATER FOR AEROSOL GENERATING DEVICE AND DEVICE

(71) Applicant: NICOVENTURES TRADING LIMITED, London (GB)

(72) Inventors: Mark Potter, London (GB); Ugurhan Yilmaz, London (GB); Geoffrey Foss-Smith, London (GB)

(73) Assignee: Nicoventures Trading Limited, London (GB)

( * ) Notice: Subject to any disclaimer, the term of this patent is extended or adjusted under 35 U.S.C. 154(b) by 262 days.

(21) Appl. No.: 16/646,418

(22) PCT Filed: Sep. 10, 2018

(86) PCT No.: PCT/EP2018/074350
§ 371 (c)(1),
(2) Date: Mar. 11, 2020

(87) PCT Pub. No.: WO2019/048685
PCT Pub. Date: Mar. 14, 2019

(65) Prior Publication Data
US 2020/0268052 A1  Aug. 27, 2020

(30) Foreign Application Priority Data
Sep. 11, 2017 (GB) .................... 1714564

(51) Int. Cl.
*A24F 13/00* (2006.01)
*A24F 17/00* (2006.01)
(Continued)

(52) U.S. Cl.
CPC ............. *A61M 16/06* (2013.01); *A24F 40/44* (2020.01); *A24F 40/46* (2020.01); *H05B 1/0297* (2013.01); *H05B 3/06* (2013.01); *A24F 40/10* (2020.01)

(58) Field of Classification Search
CPC .......... A24F 40/10; A24F 40/44; A24F 40/46; A61M 11/042; A61M 15/06; A61M 16/06; H05B 1/0297; H05B 3/06
See application file for complete search history.

(56) References Cited

U.S. PATENT DOCUMENTS 10,701,974 B2 * 7/2020 Rosser ................. A61M 11/042
2011/0155153 A1   6/2011 Thorens
(Continued)

FOREIGN PATENT DOCUMENTS

CN    104540406 A    4/2015
CN    204232305      4/2015
(Continued)

OTHER PUBLICATIONS

International Search Report, Application No. PCTZEP2018/074350, dated Jan. 16, 2019, 3 pages.
(Continued)

*Primary Examiner* — Abdullah A Riyami
*Assistant Examiner* — Thang H Nguyen
(74) *Attorney, Agent, or Firm* — Patterson Thuente, P.A.

(57) ABSTRACT

A heater for use in an aerosol generating device is disclosed. The heater includes a heating element comprising a coil. The coil has at least two coiled regions and one non-coiled region. The heater includes a pair of wicks arranged to feed e-liquid to the heating element from different directions. A device for generating an inhalable medium including a heater for volatilizing liquid is also disclosed.

22 Claims, 4 Drawing Sheets

(51) Int. Cl.
*A24F 25/00* (2006.01)
*A61M 16/06* (2006.01)
*A24F 40/46* (2020.01)
*A24F 40/44* (2020.01)
*H05B 1/02* (2006.01)
*H05B 3/06* (2006.01)
*A24F 40/10* (2020.01)

(56) References Cited

U.S. PATENT DOCUMENTS

| | | | | |
|---|---|---|---|---|
| 2013/0192623 | A1* | 8/2013 | Tucker | H05B 1/0244 131/329 |
| 2013/0213419 | A1* | 8/2013 | Tucker | H05B 3/34 131/328 |
| 2014/0000638 | A1* | 1/2014 | Sebastian | A24F 40/50 131/328 |
| 2014/0209105 | A1* | 7/2014 | Sears | A24F 40/44 131/328 |
| 2014/0366898 | A1* | 12/2014 | Monsees | A24F 40/30 131/329 |
| 2015/0144145 | A1* | 5/2015 | Chang | A24F 40/42 131/328 |
| 2015/0216237 | A1* | 8/2015 | Wensley | A61M 15/002 131/273 |
| 2015/0245659 | A1* | 9/2015 | DePiano | B21D 53/06 392/397 |
| 2017/0188635 | A1* | 7/2017 | Force | H05B 1/0244 |

FOREIGN PATENT DOCUMENTS

| | | |
|---|---|---|
| CN | 105473012 A | 4/2016 |
| CN | 106231932 A | 12/2016 |
| GB | 476814 A | 12/1937 |
| RU | 2629882 C2 | 9/2017 |
| WO | WO 2016059000 | 4/2016 |
| WO | WO 2016065522 | 5/2016 |

OTHER PUBLICATIONS

Decision to Grant dated Jan. 25, 2021 for Russian Application No. 2020110232, 9 pages.
First Office Action and Search Report for Chinese Patent Application No. 2018800585844, dated Jan. 27, 2022, 10 pages.
International Preliminary Report on Patentability for Application No. PCT/EP2018/074350 dated Dec. 10, 2019, 7 pages.
Written Opinion for Application No. PCT/EP2018/074350, dated Jan. 16, 2019, 7 pages.

* cited by examiner

HEATER FOR AEROSOL GENERATING DEVICE AND DEVICE

PRIORITY CLAIM

The present application is a National Phase entry of PCT Application No. PCT/EP2018/074350, filed Sep. 10, 2018, which claims priority from GB Patent Application No. 1714564.0, filed Sep. 11, 2017, each of which is hereby fully incorporated herein by reference.

TECHNICAL FIELD

The present disclosure relates to a heater for an aerosol generating device.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are so-called e-cigarette devices. These devices typically contain a liquid which is heated to vaporize the liquid to produce an inhalable vapor and/or aerosol. The liquid may contain nicotine and/or flavorings and/or aerosol-generating substances, such as glycerol. The known e-cigarette devices typically do not contain or use tobacco.

Other examples are heating devices which release compounds by heating, but not burning, the material. The material may be for example tobacco or other non-tobacco products, which may or may not contain nicotine.

Devices that heat liquid during use often have wicks for wicking liquid from a liquid storage to a heater. In certain known devices the heater is proximal to the wick, occasionally in the form of a coil. In some cases, the heater and wick arrangement results in the wick drying out and become burnt. If the wick becomes burnt, a user must replace the wick which increases the expense of maintaining the device.

SUMMARY

According to a first aspect of the present disclosure, there is provided a heater for use in an aerosol generating device, the heater comprising: a heating element, the heating element comprising a coil, the coil having at least two coiled regions and one non-coiled region; and at least two wicking regions, wherein each wicking region is arranged to feed a liquid to the heating element to be heated and wherein a first wicking region of the at least two wicking regions feeds liquid to the heating element along a different pathway to that of a second wicking region of the at least two wicking regions.

In an embodiment, at least one of the first and second wicking regions is arranged at least partially within at least one of the at least two coiled regions.

In an embodiment, the first and second wicking regions are arranged so as to be substantially parallel to one another.

In an embodiment, the first wicking region is arranged at least partially within a first of the at least two coiled regions and the second wicking region is arranged at least partially within a second of the at least two coiled regions.

In an embodiment, the at least two coiled regions and one non-coiled region are arranged to substantially form a U-shape.

In an embodiment, the first wicking region and the second wicking region are arranged so as to form a substantially cross shape.

In an embodiment, the first wicking region and the second wicking region are separated from each other and each is substantially L shaped.

In an embodiment, at least a part of the first wicking region is arranged within a first of the plurality of coiled regions and at least a part of the second wicking region is arranged within a second of the plurality of coiled regions.

In an embodiment, the first wicking region and the second wicking region are regions of a unitary wick body.

In an embodiment, a first part of the first wicking region is arranged within a first of the plurality of coiled regions and a second part of the first wicking region is arranged within a second of the plurality of coiled regions and the second wicking region extends substantially transverse to the first wicking region across the non-coiled region.

In an embodiment, one of the at least two coiled regions is at least one of vertically and horizontally misaligned with another of the at least two coiled regions.

In an embodiment, the at least two coiled regions of the coil are non-identical.

In an embodiment, one of the at least two coiled regions has a different heat rate to another of the at least two coiled regions.

In an embodiment, one of the at least two coiled regions has a different heat flux density to another of the at least two coiled regions.

In an embodiment, wherein the non-coiled region is arranged between the at least two coiled regions.

In an embodiment, comprising a gap between the first and second wicking regions, wherein the non-coiled region of the coil traverses the gap.

In an embodiment, the first and second wicking regions are separate components of at least two separate wicks.

According to a second aspect of the present disclosure, there is provided a heater for use in an aerosol generating device, the heater comprising: a heating element, the heating element comprising a coil, the coil having at least two coiled regions and one non-coiled region; and a wick arranged within the at least two coiled regions with a central region of the wick substantially free of either coiled region.

In an embodiment, the central portion of the wick is proximal to the non-coiled region and the at least two coiled regions are arranged substantially equally either side of the central portion of the wick.

In an embodiment, the at least two coiled regions of the coil are non-identical.

In an embodiment, one of the at least two coiled regions has a different heat rate to another of the at least two coiled regions.

In an embodiment, one of the at least two coiled regions has a different heat flux density to another of the at least two coiled regions.

In an embodiment, the central region of the wick is substantially co-incident with the non-coiled region.

According to a third aspect of the present disclosure, there is provided a device for generating an inhalable medium, the device comprising: a container for holding a liquid; a heater according to a first aspect of the present disclosure; and an outlet; the device being such that, in use, liquid drawn from the container by the at least two wicking regions and volatilized by the heating element passes out of the outlet in the form of at least one of a vapor and an aerosol.

According to a third aspect of the present disclosure, there is provided a device for generating an inhalable medium, the device comprising: a container for holding a liquid; a heater according to a second aspect of the present disclosure; an outlet; the device being such that, in use, liquid drawn from the container by the wick and volatilized by the heating element passes out of the outlet in the form of at least one of a vapor and an aerosol.

DETAILED DESCRIPTION

Figure 1:
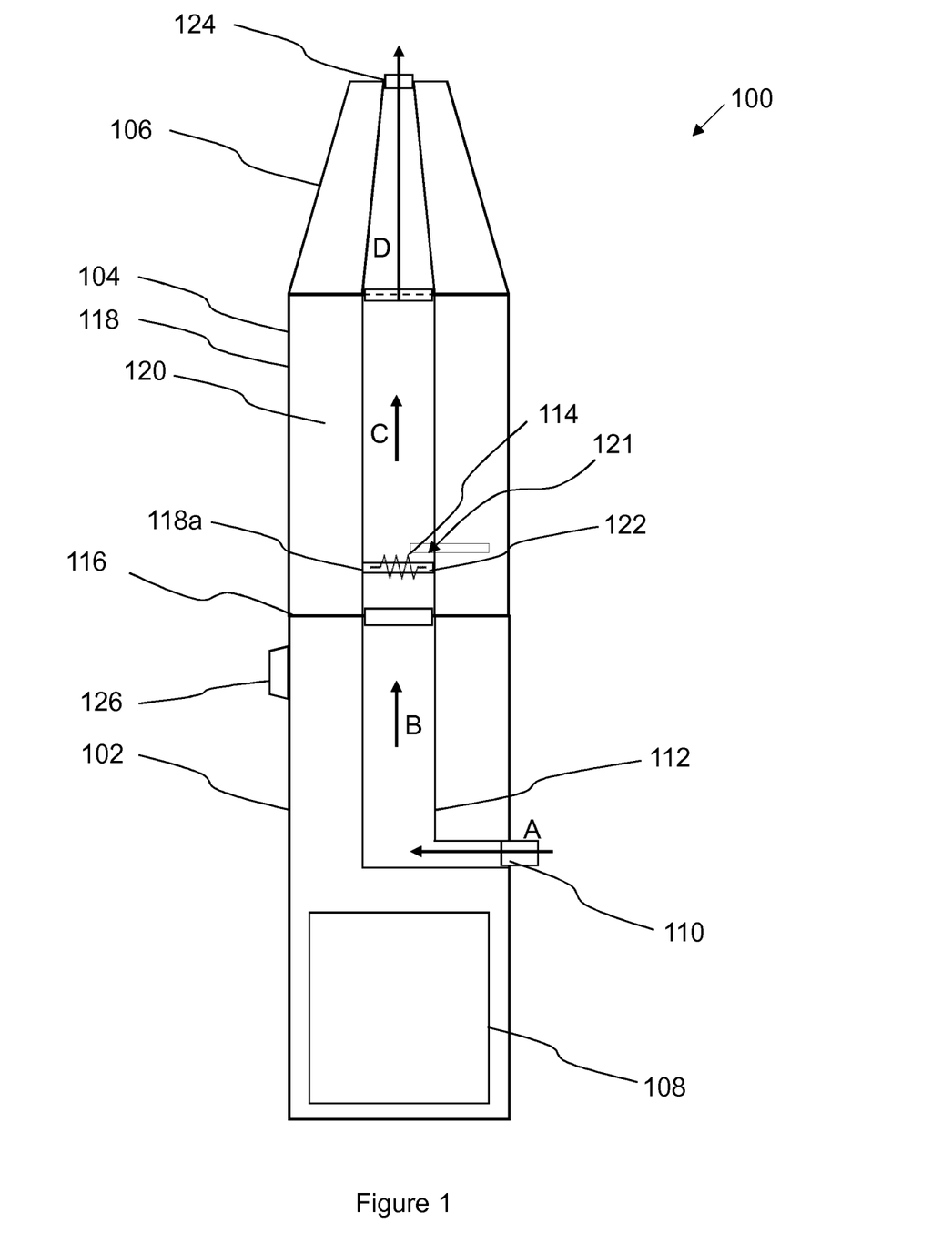
FIG. 1 illustrates a schematic cross section of a first aerosol generating device according to a first example.

Referring to FIG. 1, a schematic of an example aerosol generating device 100 according to a first example, is illustrated. The aerosol generating device 100 is an inhalation device (i.e. a user uses it to inhale an aerosol provided by the device). The aerosol generating device 100 is handheld.

The device 100 comprises a body 102 housing a power source 108 such as a battery 108.

The device 100 comprises a container 104. In this example, the container 104 is an aerosol generating article or cartridge 104 that is removable from the overall device 100. The cartridge 104 may therefore be installed, removed, or replaced in the device 100. The cartridge 104 comprises a connecting portion 116 for releasably connecting the cartridge 104 to the body 102 of the device 100. The cartridge 104 comprises a liquid container 118 for containing a liquid 120, and a heating arrangement 121. The heating arrangement 121, which is illustrated schematically only in FIG. 1, comprises at least one wick 122 for drawing the liquid 120 from the liquid container 118 and a heating element 114 for heating the liquid drawn by the at least one wick. The heating element 114 comprises a coil having at least two coiled regions (not shown in FIG. 1) and one non-coiled region (not shown in FIG. 1). Different examples of the heating arrangement 121 that may be used in the device 100 will be described in more detail below.

The device 100 comprises a mouthpiece 106 on which a user (not shown) can draw. The mouthpiece 106 is removeably connected to the cartridge 104. The mouthpiece defines an outlet 124 for egress of inhalable medium.

In broad outline, in the device 100 of FIG. 1, inlet air from an air inlet 110 in the body 102 enters the device 100. The at least one wick 122 of the heating arrangement 121 draws in liquid 120 from the liquid container 118, and the liquid 120 is heated by the heating element of the heating arrangement 121 to volatilize the liquid 120 thereby to generate a flow of at least one of a vapor and an aerosol. The flow of vapor or aerosol passes through the channel 112 and exits through the outlet 124 for inhalation by a user.

In this respect, first it may be noted that, in general, a vapor is a substance in the gas phase at a temperature lower than its critical temperature, which means for example the vapor can be condensed to a liquid by increasing its pressure without reducing the temperature. On the other hand, in general, an aerosol is a colloid of fine solid particles or liquid droplets, in air or another gas. A colloid is a substance in which microscopically dispersed insoluble particles are suspended throughout another substance.

For reasons of convenience, as used herein the term aerosol should be taken as encompassing an aerosol, a vapor or a mixture of an aerosol and vapor.

Returning to FIG. 1, the device 100 defines a flow path (illustrated schematically in FIG. 1 by arrows A to D) from the air inlet 110 in the body 102 of the device 100, via a channel 112 defined through the device 100, to the inhalable medium outlet 124 defined in the mouthpiece 106.

The heating arrangement 121 is located in a portion of the channel 112 defined by the cartridge 104 of the device 100, the channel 112 extending from the air inlet 110 of the body 102 to the outlet 124.

The heating element 114 of the heating arrangement 121 is (electrically) connected to the battery 108 to allow the heating element 114 to be powered. The heating element 114 may be controlled to be powered, for example, by a user pressing or interacting with a button or interface 126 of the body 102 of the device 100, and/or by a puff detector (not shown) of the overall device 100.

In this example, the heating arrangement 121 is located in the flow path (A-D), that is, the heating arrangement 121 partially interrupts the flow path (A-D) such that the inlet air passes through, over and/or around the heating arrangement 121. This may allow effective and/or efficient entraining of volatilized components following heating of the at least one wick 122 by the heating element 114.

In this example, the liquid container 118 is generally annular in shape, and defines a portion of the channel 112 running through the length of the liquid container 118. The channel 112 defines at least a portion of the first flow path (A-D). The liquid container 118 may be formed of rigid, watertight and airtight materials, such as metal, suitable plastics, etc.

The at least one wick 122 is in contact with the liquid 120. This may be achieved for example by the at least one wick 122 being inserted through a through hole (not shown) in a wall 118a of the liquid container 118. Alternatively or additionally, a portion of the wall 118a defining the channel 112 may be a porous member which allows liquid 120 to pass through from the liquid container 118, and the at least one wick 122 may be in contact with the porous wall 118a. The wall 118a may be for example in the form of a porous annulus. A porous wall 118a of this type may help to regulate the flow of liquid 120 onto the wick 122. The at least one wick 122 is generally absorbent and acts to draw in liquid 120 from the liquid container 118 by capillary action. The wick 122 can be non-woven.

The at least one wick 122 extends across the channel 112. For example, the at least one wick 122 may extend over substantially all of a cross section of the channel 112. The at least one wick 122 may be or comprise a mesh (not shown), and may, for example, be formed of or comprise a metal mesh (not shown). Apertures (not shown) defined by the mesh (not shown) may allow heated air to flow through and around the mesh (not shown), thereby to volatilize the liquid 120 from the mesh to form an aerosol. The liquid 120 from the liquid container 118 may be drawn into the channel 112, by the mesh (not shown), for example by capillary action. Alternatively or additionally, the at least one wick 122 may be or comprise for example a cotton or wool material or the like, or a synthetic material, including for example polyester, nylon, viscose, polypropylene or the like, or a ceramic material.

The at least one wick 122 may be supported in the channel 112 by a supporting element (not shown) that fixes and supports the wick 122 against the liquid container 118. This may help ensure the at least one wick 122 does not move during use.

Figure 2:
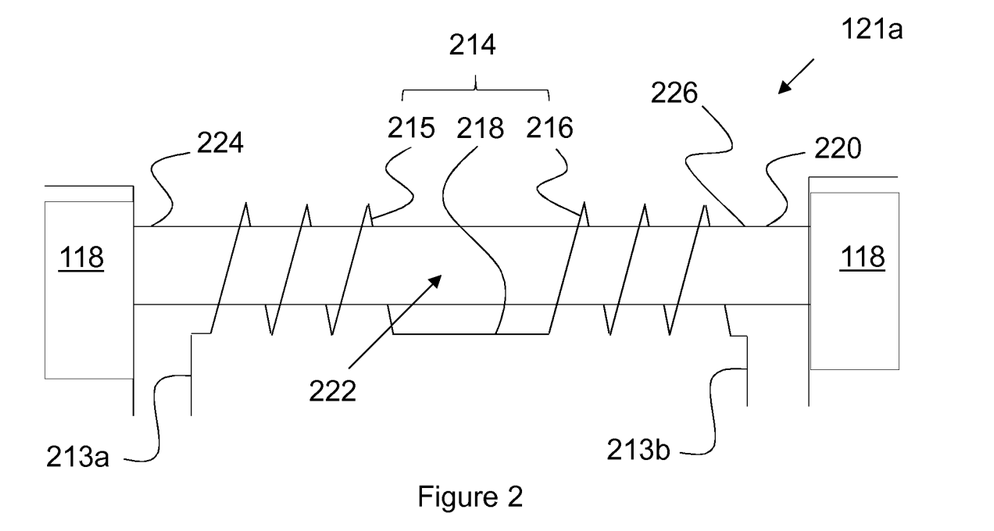
FIG. 2 illustrates a schematic front on view of a heater according to a first example.

FIG. 2 illustrates a first example of a heating arrangement 121a that can be used as the heating arrangement 121 in the device 100. The heating arrangement 121a comprises a heating element 214 and a wick 222. The heating element 214 is a coil formed of an electrically conductive wire and comprises first 215 and second 216 coiled regions joined by a non-coiled region 218 (i.e. a region in which the wire is not wound). At each end of the heating element 214, the first 215 and second 216 coiled regions each comprises a respective connecting element 213a, 213b which connect the heating element 214 to the power source 108 in the device 100 to power the heating element 214.

In the specific example shown, the heating element 214 has two coiled regions 215, 216 and one non-coiled region 218. In other examples, the heating element 214 may have more than two coiled regions 215, 216 and more than one non-coiled region 218.

The wick 220 is arranged within the coiled regions 215, 216 with a central region 222 of the wick 220 substantially co-incident with the non-coiled region 218. In the example shown in FIG. 2, the wick 220 has at least two wicking regions 224, 226 wherein each wicking region 224, 226 is arranged to feed a liquid to the heating element 214 to be heated. The wicking regions 224, 226 can be seen to feed liquid to the heating element 214 along different pathways.

In the example shown, the first 215 and second 216 coiled regions are arranged substantially half-way between the central region 222 of the wick 220 and the liquid container 118 of, for example, device 100 with which each end of the wick 220 is in fluid communication with. In another arrangement the coiled regions 215, 216 may be arranged non-symmetrically either side of a central region 222 of the wick 220. Each end of the wick 220 projects into the liquid container 118 through a hole in the liquid container 118.

Liquid from the liquid container 118 flows along the wick 220 and is vaporized in portions of the wick near the first 215 and second 216 coiled regions. Some liquid will not be vaporized and flow through to the central region 222 of the wick 220. The central region 222 of the wick 220 therefore may act as a liquid reservoir for liquid that has flowed to the central region 222 of the wick 220 and not been vaporized near the first 215 and second 216 coiled regions. This provides a further means of avoiding drying out of the wick 220.

In other examples, the first 215 and second 216 coiled regions are arranged towards the container 118 or may be arranged towards the central region 222 of the wick 220. The first 215 and second 216 coiled regions may be arranged asymmetrically either side of the non-coiled region 218. The length of the non-coiled region 218 may be equal to, less than or substantially equivalent to the length of one of the first 215, and second 216 coiled regions.

The first 215 and second 216 coiled regions in the example shown have substantially the same number of loops in the wire of the heating element 214 and cover substantially same-size portions of the wick 220. In other examples, one coiled region 215, 216 has a greater number of loops than the other coiled region 215, 216. In an example, one coiled region 215, 216 covers a greater portion of the wick 220 than the other coiled region 215, 216. In any of the examples described herein, one coiled region 215, 216 may be arranged non-identically with respect to another coiled region 215, 216 of the heating element 214.

One coiled region 215, 216, in use, may cause a certain heat rate or flux to be delivered to the wick 220, the heat rate or flux being different to that caused by another coiled region 215, 216. One coiled region 215, 216 may have a different highest heat rate or flux at any one point of the coiled region 215, 216 compared to another coiled region 215, 216. One coiled region 215, 216 may have a different highest heat flux density at any one point of the coiled region 215, 216 compared to another coiled region 215, 216. For example, any of the following traits inter alia may differ between the coiled regions 215, 216, or even within a coiled region 215, 216, to achieve a non-identical nature between coiled regions 215, 216: the number of loops in a coiled region 215, 216; the radius of loop or loops, provided the loop has at least a minimum radius of greater than the radius of the wick; the distance between loops; the thickness of wire in a loop; and, the shape of loop.

The first 215 and second 216 coiled regions of the heating element 214 accommodate portions of the wick 220. Advantageously, the likelihood of the wick 220 drying out or becoming burnt during use is reduced compared with some known arrangements because the central region 222 of the wick 220 is not surrounded by a coiled region 215, 216 of the heating element 214. The non-coiled region 218 of the coil helps prevent an over concentration of heat energy from the heating element 214 occurring in the central region 222 of the wick 220. Instead, the heat energy is dispersed more evenly along the length of the wick 220.

In use, liquid held in the container 118 of, for example, device 1 is wicked towards the coiled regions 215, 216 of the heating element 214 and is heated. The liquid may become volatilized at this point and a passing airflow will entrain the compounds prior to inhalation by a user. The central region 222 of the wick 220 does not dry out, as mentioned above, but rather holds liquid which has been drawn from the container 118. This liquid has been heated during its passage to the central region 222 of the wick 220 and is held in the central region 222 prior to volatilization. The central region 222 is heated by the heating element 214 but without a concentration of heat energy on a small area, as described above. Preventing this concentration of heat energy at one portion of the wick 220 prevents the wick 220 drying out, becoming burnt and unusable. In turn, this reduces the frequency with which the wick 220 must be replaced. In turn, this reduces the operating cost for the user.

In the example shown in FIG. 2, the coiled regions 215, 216 of the heating element 214 are arranged so that the longitudinal axes projecting through the center of the coiled regions 215, 216 are substantially aligned. The direction of projection of the non-coiled region 218 is substantially parallel to the longitudinal axes of the coiled regions 215, 216. In other examples, the longitudinal axes projecting through the center of the coiled regions 215, 216 are not aligned and may have an offset. The coiled regions 215, 216 may be arranged so as to be at least one of horizontally or vertically misaligned.

The heat energy delivered to the wick 220 by the heating element 214, as shown in FIG. 2, will be focused at the center of the two coiled regions 215, 216 of the heating element 214. As mentioned above, the two coiled regions 215, 216 are arranged towards the container 118. The locations of highest concentration of heat energy is therefore closer to the feed of liquid from the container 118. This, in turn, further reduces the likelihood of the wick 220 in those locations drying out and becoming burnt.

The non-coiled region 218 in FIG. 2 is shown as a straight section of the heating element 214. In other examples, the non-coiled region is not coiled but not straight. The non-coiled region 218 may be any of curved, angled, wavy, sinusoidal, jagged, straight or substantially straight. The non-coiled region 218 has a heat rate which is less than the coiled regions 214, 216.

Figure 3A:
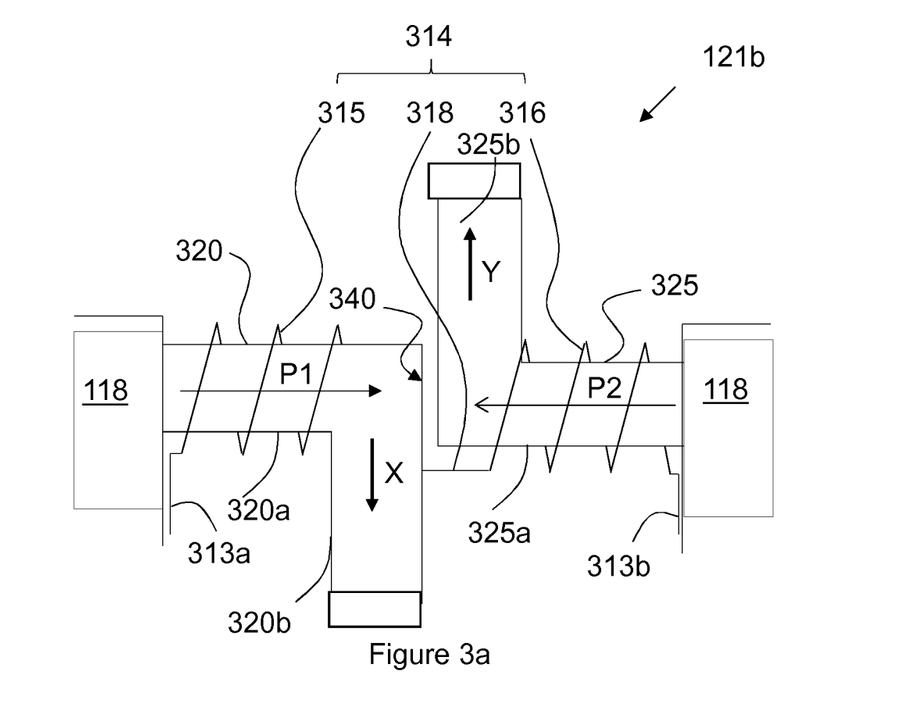
FIG. 3a illustrates a schematic front on view of a second heater according to a second example.

FIG. 3a illustrates a second example of a heating arrangement 121b that can be used as the heating arrangement 121 in the device 100. The heating arrangement 121b is similar in some respects to the heating arrangement 121a described with reference to FIG. 2, but comprises a plurality of wicks 320, 325 having a plurality of wicking regions 320a, 320b, 325a, 325b, instead of a single wick having a plurality of wicking areas. In this example, the heating arrangement 121b comprises a first wick 320 and a second wick 325. For brevity, features in FIG. 3a and the functions thereof that are the same as those features already described with reference to FIG. 2 are given similar reference numerals to those in FIG. 2 but increased by 100, and will not be described in detail again.

As illustrated in the example shown in FIG. 3a, each of the wicks 320, 325 is in fluid communication with the container 118 of the aerosol generating device 100 and are arranged to feed e-liquid to the coil of the heating element 314 along different paths (labeled P1 and P2, respectively).

In this example, the first wick 320 and the second wick 325 are both substantially 'L' shaped and comprise respective first wicking regions 320a, 325a and second wicking regions 320b, 325b substantially perpendicular to the first wicking regions 320a, 325a. Each of the first wick 320 and the second wick 325 may be, for example, circular in cross section.

A first coiled region 315 of the coil of the heating element 314 is arranged around the first wicking region 320a of the first wick 320 and the second coiled region 316 of the coil of the heating element 314 is arranged around the first wicking region 325a of the second wick 325.

The first 320 and second 325 wicks shown in FIG. 3a, are arranged in a substantially cross-shape configuration. That is to say, the first 320 and second 325 wicks are opposing each other with their respective second wicking regions 320b, 325b directed in opposite directions X, Y to each other.

The first 320 and second 325 wicks may be threaded through the coil of the heating element 314 in different directions and from different ends to achieve such a configuration, or a substantially similar configuration. The configuration shown causes liquid to be supplied to the heating element 314 along two different pathways such that an increased total quantity of liquid reaches the heating element 314. By increasing the total flow of liquid to the heating element 314 through the first 320 and second 325 wicks the likelihood of a wick 320, 325 drying out and becoming burnt is reduced.

Furthermore, by using multiple wicks 320, 325 and increasing the flow of liquid from the container 118, more heat energy can be delivered to the wicks 320, 325 e.g. by a more powerful heating element 314 while reducing the likelihood of the wicks 320, 325 drying out. By preventing the drying out of the wicks 320, 325, there is a reduced chance of burning the wicks 320, 325. Enabling use of a more powerful heating element 314 results in a greater amount of vaporization which allows the user to perceive an organoleptic effect more rapidly or more intensely. The ends of the wicks 320, 325 that are not shown may be connected to the liquid container 118 to increase liquid flow.

In this example, there is a space or gap 340 arranged between the first 320 and second 325 wicks. In the example shown in FIG. 3a, the wicks 320, 325 nearly meet at the gap 340 and the non-coiled region 318 of the coil of the heating element 314 traverses the gap 340. In this configuration, the non-coiled region 318 enables the first 315 and second 316 coiled regions of the heating element 314 to be arranged around the first 320 and second 325 wicks, respectively.

As explained above, the wicks 320, 325 are arranged to diverge at the gap 340 and project in different directions. In the specific example shown, the first wick 320 projects in a direction X at the gap 340 and the second wick 325 projects in direction Y. Direction X is antiparallel to direction Y. In another example, direction X may be parallel to direction Y or at some angle to direction Y.

In another example, the first 320 and second wicks 325 are in the arrangement shown in FIG. 3a; however there is no gap 340 between the wicks 320, 325. The first wick 320 abuts the second wick 325. This connection between the first wick 230 and second wick 325 promotes liquid flow between the wicks 230, 235, and therefore promotes liquid flow from the container 118.

Figure 3B:
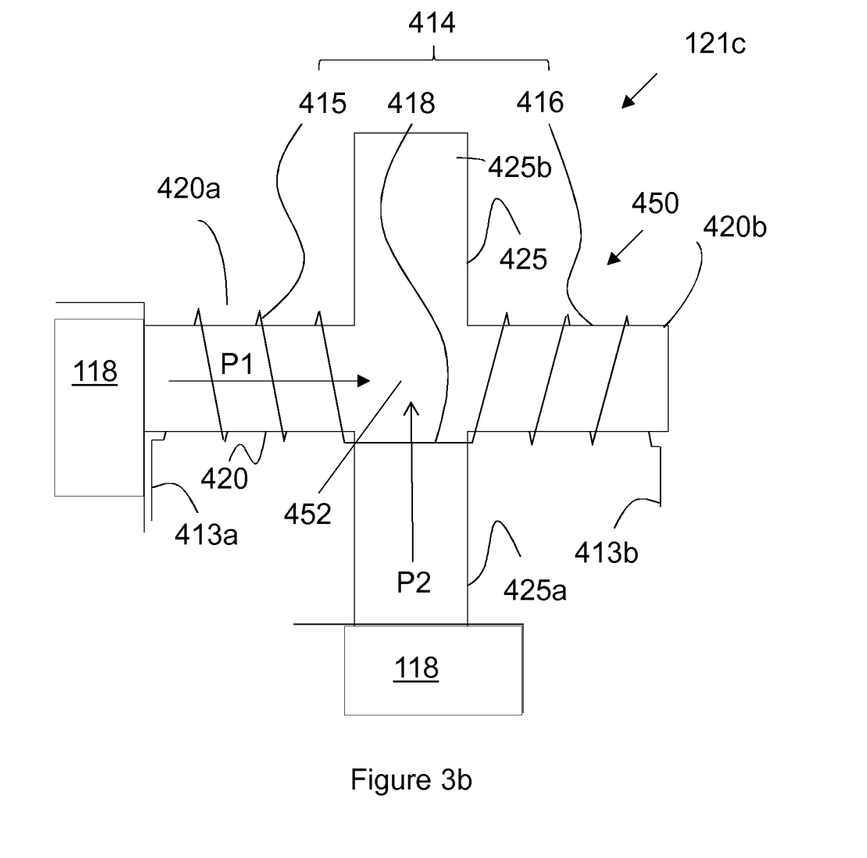
FIG. 3b illustrates a schematic front on view of a third heater according to a third example.

FIG. 3b, illustrates a third example of a heating arrangement 121c that can be used as the heating arrangement 121 in the device 100. The heating arrangement 121c is similar in some respects to the heating arrangement 121b described with reference to FIG. 3a, but comprises a unitary wick body 450 comprising first 420 and second 425 wicks rather than separate wicks. For brevity, features in FIG. 3b and the functions thereof that are the same as those features already described with reference to FIG. 3a are given the same reference numerals to those in FIG. 3a but increased by 100, and will not be described again. The unitary wick body 450 has a substantially cross-shape configuration defined by the first wick 420 and the second wick 425. The first wick 420 comprises a first wicking region 420a and a second wicking region 420b and the second wick 425 comprises a first wicking region 425a and a second wicking region 425b. The first wick 420 and the second wick 425 are arranged substantially perpendicular to each other and share a common central portion 452 of the unitary wick body 450.

A first coiled region 415 of the coil of the heating element 414 is arranged around the first wicking region 420a of the first wick 420 and the second coiled region 416 of the coil of the heating element 414 is arranged around the second wicking region 420b of the first wick 420. The non-coiled region 418 of the coil of the heating element 414 connects the first coiled region 415 and the second coiled region 416 across the central portion 452 of the unitary wick body 450.

The first wick 420 and the second wick 425 are each in fluid communication with the container 118 of the aerosol generating device 100 and are arranged to feed e-liquid to the coil of the heating element 414 along different paths (labeled P1 and P2, respectively).

As with the example illustrated in FIG. 3a, this configuration causes liquid to be supplied to the heating element 414 along two different pathways such that an increased total quantity of liquid reaches the heating element 414. By increasing the total flow of liquid to the heating element 414 through the first 420 and second 425 wicks the likelihood of a wick 420, 425 drying out and becoming burnt is reduced and a relatively powerful heating element can be utilized.

Figure 4:
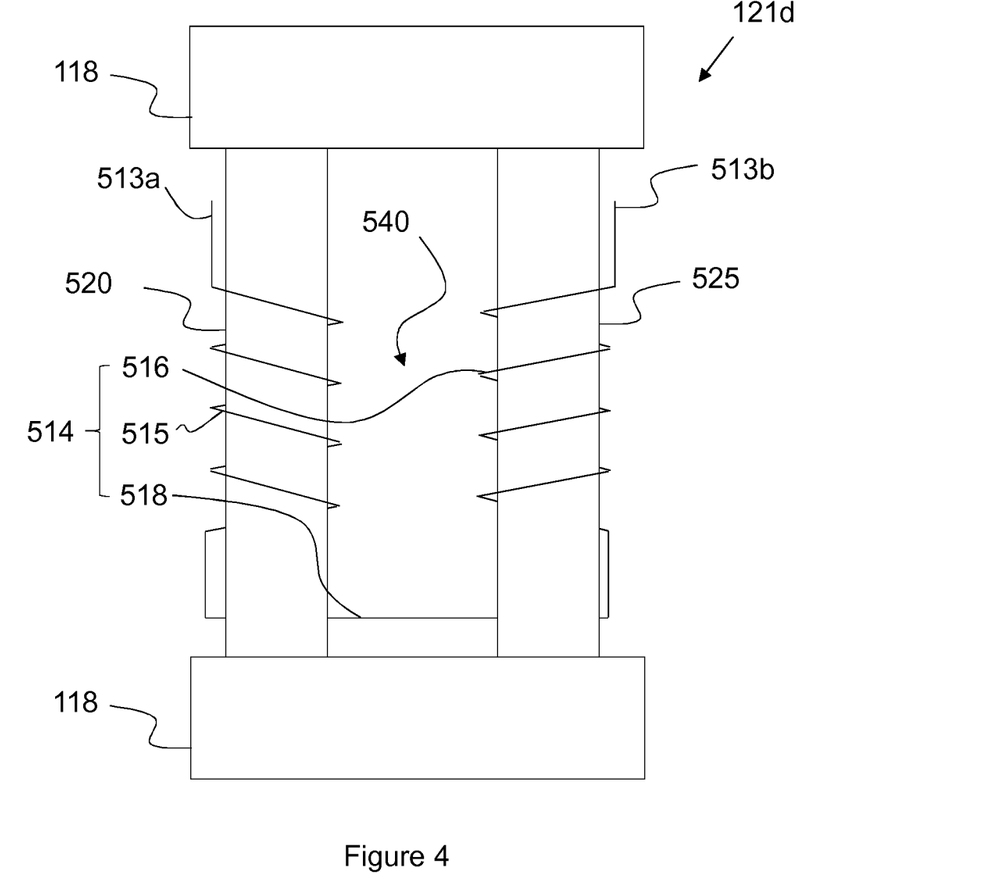
FIG. 4 illustrates a schematic front on view of a fourth heater according to a fourth example.

FIG. 4 illustrates a fourth example of a heating arrangement 121d that can be used as the heating arrangement 121 in the device 100. The heating arrangement 121d is similar in some respects as the heating arrangement 121b described with reference to FIG. 3a, but has a different arrangement of multiple wicks 520, 525 and heating element 514. For brevity, features in FIG. 4 and the functions thereof that are the same as those features already described with reference to FIG. 3a are given the same reference numerals to those in FIG. 3a but increased by 200, and will not be described again.

The heating arrangement 121d comprises a heating element 514 and a first 520 and a second 525 wicks. The heating element 514 is a coil formed of an electrically conductive wire and comprises first 515 and second coiled regions 516 joined by a non-coiled region 518.

In this example, the first coiled region 515 and the second coiled region 516 are arranged so that the longitudinal axes projecting through the center of the coiled regions 515, 516 are substantially parallel. The direction of projection of the non-coiled region 518 is substantially perpendicular to the longitudinal axes of the coiled regions 515, 516. In other examples, the longitudinal axes projecting through the center of the coiled regions 515, 516 need not be parallel and may instead be at an angle to one another. The first 515 and second 516 coiled regions may be arranged so as to be at least one of horizontally or vertically misaligned.

The first wick 520 is arranged within the first coiled region 515 and the second wick 525 is arranged within the second coiled region 516. In this example, each of the wicks 520, 525 is substantially cylindrical in shape, and they are substantially aligned with each. As is schematically illustrated in FIG. 4, each of the ends of the wicks 520, 525 is in fluid communication with the interior of the liquid container 118 of the device 100. The greater the total contact between the wicks 520, 525 and the liquid in the liquid container 118, the greater the flow rate of liquid to the wicks 520, 525. Each of the wicks 520, 525 has at least one wicking region, as previously described. In the example show, a wicking region of the first wick 520 may be parallel to a wicking region of the second wick 525.

In this example the first 515 and second 516 coiled regions (and hence the first 520 and second 525 wicks) are substantially parallel. In other examples, the first 515 and second 516 regions (and hence the first 520 and second 525 wicks) may be at an angle with respect to each other (i.e. not substantially parallel).

A gap 540 between the first 520 and second 525 wicks is traversed by the non-coiled region 518 of the heating element 514. Accordingly, the first 515 and second 516 coiled regions and the non-coiled region 418 are arranged to substantially form a U-shape.

The heating element 54 may be made of a length of thermally conductive material, such as ceramics or metals for example copper, aluminum, kanthal or other alloys.

The above embodiments are to be understood as illustrative examples of the disclosure. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

The invention claimed is:

1. A heater for use in an aerosol generating device, the heater comprising: a heating element, the heating element comprising a coil, the coil having at least two coiled regions and one non-coiled region; and
at least a first wick comprising at least two wicking regions, wherein each of the at least two wicking regions is arranged to feed a liquid to the heating element to be heated, wherein a first wicking region of the at least two wicking regions feeds liquid to the heating element along a different pathway than that of a second wicking region of the at least two wicking regions, and wherein the first wick comprises a gap between the first wicking region and the second wicking region, wherein the non-coiled region of the coil traverses the gap.

2. The heater according to claim 1, wherein at least one of the first wicking region or the second wicking region is arranged at least partially within at least one of the at least two coiled regions.

3. The heater according to claim 1, further comprising a second wick, wherein the first wick and the second wick are arranged so as to be substantially parallel to one another.

4. The heater according to claim 1, wherein the first wicking region is arranged at least partially within a first of the at least two coiled regions and the second wicking region is arranged at least partially within a second of the at least two coiled regions.

5. The heater according to claim 1, wherein the at least two coiled regions and one non-coiled region are arranged to substantially form a U-shape.

6. The heater according to claim 1, further comprising a second wick comprising at least two wicking regions, wherein the first wick and the second wick are arranged so as to form a substantially cross shape.

7. The heater according to claim 6, wherein the first wick and the second wick are separated from each other and each is substantially L shaped.

8. The heater according to claim 7, wherein at least a part of the first wicking region of the first wick is arranged within a first of the at least two coiled regions and at least a part of the second wicking region of the first wick is arranged within a second of the at least two coiled regions.

9. The heater according to claim 6, wherein the first wicking region and the second wicking region are regions of a unitary wick body.

10. The heater according to claim 1, wherein one of the at least two coiled regions is at least one of vertically or horizontally misaligned with another of the at least two coiled regions.

11. The heater according to claim 1, wherein the at least two coiled regions of the coil are non-identical.

12. The heater according to claim 1, wherein one of the at least two coiled regions has a different heat rate than another of the at least two coiled regions.

13. The heater according to claim 1, wherein one of the at least two coiled regions has a different heat flux density than another of the at least two coiled regions.

14. The heater according to claim 1, wherein the non-coiled region is arranged between the at least two coiled regions.

15. The heater according to claim 1, wherein the first wicking region and the second wicking region are separate components of at least two separate wicks.

16. A device for generating an inhalable medium, the device comprising:
a container for holding a liquid;
the heater according to claim 1; and
an outlet;
the device being such that, in use, liquid drawn from the container by the at least two wicking regions and volatilized by the heating element passes out of the outlet in the form of at least one of a vapor or an aerosol.

17. A heater for use in an aerosol generating device, the heater comprising:
   a heating element, the heating element comprising a coil, the coil having at least two coiled regions and one non-coiled region; and
   a wick arranged within the at least two coiled regions with a central region of the wick substantially free of either of the at least two coiled regions;
wherein the central region of the wick is proximal to the non-coiled region and the at least two coiled regions are arranged substantially equally on either side of the central region of the wick.

18. The heater according to claim 17 any, wherein one of the at least two coiled regions has a different heat rate than another of the at least two coiled regions.

19. The heater according to claim 17, wherein one of the at least two coiled regions has a different heat flux density than another of the at least two coiled regions.

20. The heater according to claim 17, wherein the central region of the wick is substantially co-incident with the non-coiled region.

21. A device for generating an inhalable medium, the device comprising:
   a container for holding a liquid;
   the heater according to claim 17;
   an outlet;
   the device being such that, in use, liquid drawn from the container by the wick and volatilized by the heating element passes out of the outlet in the form of at least one of a vapor or an aerosol.

22. A heater for use in an aerosol generating device, the heater comprising:
   a heating element, the heating element comprising a coil, the coil having at least two coiled regions and one non-coiled region; and
   at least two wicking regions, wherein each of the at least two wicking regions is arranged to feed a liquid to the heating element to be heated, wherein a first wicking region of the at least two wicking regions feeds liquid to the heating element along a different pathway than that of a second wicking region of the at least two wicking regions, and wherein a first part of the first wicking region is arranged within a first of the at least two coiled regions and a second part of the first wicking region is arranged within a second of the at least two coiled regions and the second wicking region extends substantially transverse to the first wicking region across the non-coiled region.

* * * * *

UNITED STATES PATENT AND TRADEMARK OFFICE
CERTIFICATE OF CORRECTION

PATENT NO. : 11,583,648 B2
APPLICATION NO. : 16/646418
DATED : February 21, 2023
INVENTOR(S) : Mark Potter, Urgurhan Yilmz and Geoffrey Foss-Smith Page 1 of 1

It is certified that error appears in the above-identified patent and that said Letters Patent is hereby corrected as shown below:

On the Title Page

Column 2: Under item [56] OTHER PUBLICATIONS; delete "PCTZEP2018/" and insert --PCT/EP2018/--.

In the Claims

Column 11, Line 16: Claim 18 Delete "claim 17 any," and insert --claim 17,--.

Signed and Sealed this
Sixteenth Day of July, 2024

Katherine Kelly Vidal
*Director of the United States Patent and Trademark Office*